United States Patent [19]

Helinski et al.

[11] Patent Number: 4,590,163

[45] Date of Patent: May 20, 1986

[54] BROAD HOST RANGE DNA CLONING SYSTEM FOR GRAM-NEGATIVE BACTERIA

[75] Inventors: Donald R. Helinski, La Jolla; Gary S. Ditta, Doway, both of Calif.

[73] Assignee: The Regents of the University of California, Berkeley, Calif.

[21] Appl. No.: 568,943

[22] Filed: Jan. 9, 1984

Related U.S. Application Data

[63] Continuation of Ser. No. 224,426, Jan. 12, 1981.

[51] Int. Cl.[4] .................... C12N 1/00; C12P 21/00; C12P 21/02; C12P 21/04; C12P 19/34; C12N 15/00; C12N 1/20
[52] U.S. Cl. .................................... 435/317; 435/68; 435/70; 435/71; 435/91; 435/172.3; 435/253; 435/29; 435/72; 435/73
[58] Field of Search ................. 935/29, 73; 435/68, 435/70, 91, 172.3, 253, 317

[56] References Cited

PUBLICATIONS

Ditta et al, "Broad Host Range DNA Cloning System for Gram-Negative Bacteria: Construction of a Gene Bank of *Rhizobium meliloti*", Proc, Natl. Acad. Sci. USA 77:7347 (1980).

Meyer et al, "Properties of the Plasmid RK2 as Cloning Vehicle", in *DNA Insertion Elements, Plasmids, and Episomes*, Bukhari et al (ed.), Cold Spring Harbor Laboratory, 1977, pp. 559-566.

Buchanan et al (ed.), *Bergy's Manual of Determinative Bacteriology*, Williams & Wilkins Co., Baltimore, 1974, pp. 217, 262, and 428.

Thomas et al, "Regions of Broad-Host-Range Plasmid RK2 Which Are Essential for Replication and Maintenance", J. Bacteriol. 141:213 (1980).

Figurski et al, "Replication of an Origin-Containing Derivative of Plasmid RD2 Dependent on a Plasmid Function Provided in Trans", Proc. Natl. Acad. Sci. USA 76:1648 (1979).

Guiney et al, "The DNA-Protein Relaxation Complex of the Plasmid RK2: Location of the Site-Specific Nick in the Region of the Proposed origin of Transfer", Molec. Gen. Genet. 176: 183 (1979).

Meyer et al, "Unidirectional Replication of the P—Group Plasmid RK2," Biochim. Biophys. Acta 478, 109(1977).

*Primary Examiner*—Thomas G. Wiseman
*Assistant Examiner*—James Martinell
*Attorney, Agent, or Firm*—Bertram I. Rowland

[57] ABSTRACT

Novel compositions and methods for cloning DNA in a broad range of Gram-negative bacteria. Relatively small vectors are prepared substantially free of DNA sequences coding for transfer functions, while having a broad host range replication function. While the plasmid is not self-transmissible, it is transmissible by means of a helper plasmid, which desirably has a narrow host range replication function. Exogenous DNA may be inserted into the first plasmid and conjugally transferred to the target host by means of a convenient bacterial host.

2 Claims, 2 Drawing Figures

BROAD HOST RANGE DNA CLONING SYSTEM FOR GRAM-NEGATIVE BACTERIA

The government has rights in this invention pursuant to Grant No. PFR-77-24945 awarded by the National Science Foundation and Grant No. AI-07194 awarded by the National Institute of Health.

This is a continuation of Ser. No. 224,426, filed Jan. 12, 1981.

BACKGROUND OF THE INVENTION

1. Field of the Invention

Numerous plasmid elements have been developed as cloning vehicles in *Escherichia coli*. While there have been numerous developments with *E. coli*, and numerous opportunities still remain, there will be many situations where other microorganisms will be of interest or be required for a particular purpose. In addition, the ability to transform other microorganisms will be a powerful tool in the genetic analysis of species, particularly where other genetic systems are unavailable. Furthermore, vectors could be used to augment or modify desirable characteristics of the host bacterium, such as nitrogen fixation by Rhizobium species or hydrocarbon degradation by Pseudomonas species.

A suitable vector should have a wide range of desirable properties. These properties should provide for efficient introduction of exogenous DNA, allow for high efficiency of introduction of the plasmid into the host bacteria, provide stable maintenance in exconjugants and not confer hazardous properties to the host. In addition, the plasmid should not be readily transmissible.

2. Description of the Prior Art

Meyer et al., DNA Insertion Elements, Plasmids, and Episomes, 1977, Cold Spring Harbor Laboratory, pp. 599–566, describes the properties of the plasmid RK2 as a cloning vehicle. The regions necessary for DNA replication of RK2 are described by Meyer and Helinski (1977), Biochim. Biophys. Acta. 478, 109–113, and Thomas and Helinski (1979), J. Bacteriol. 141, 213. The site for conjugal mobilizability in RK2 is described by Guiney and Helinski (1979), Mol. Gen. Genet. 176, 183–189.

SUMMARY OF THE INVENTION

Novel cloning vehicles having broad host range specificity for Gram-negative bacteria are provided. The vehicles are relatively small having one or more convenient restriction sites, normally having a single restriction site for one or more restriction enzymes. The vehicles are further characterized by being non-self-transmissible, but capable of transmission with a helper plasmid. The vehicles have a broad host range replication system and normally have a marker allowing for selection of transformants. The vehicle may be introduced into the target host either by transforming the conjugal mating host with the vehicle and the helper plasmid in a single cell or by transforming conjugal mating cells separately, so that one group of cells has the helper plasmid and another group the vehicle plasmid. A wide range of Gram-negative bacteria can be modified with exogenous DNA, while substantially ensuring the absence of transmissibility of the vehicle containing the exogenous DNA to other microorganisms.

DESCRIPTION OF THE SPECIFIC EMBODIMENTS

Figure 1:
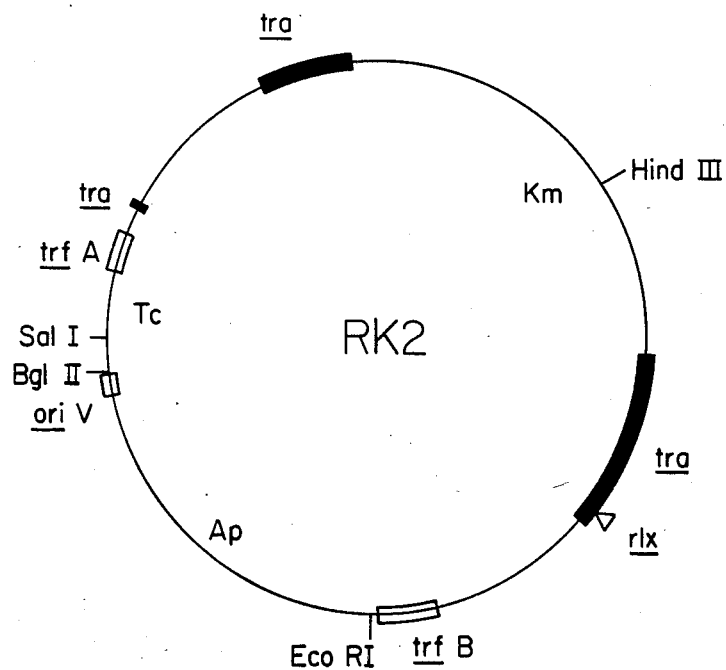
FIG. 1 is a map of RK2, where Ap, Tc and Km refer to genes conferring resistance to ampicillin, tetracycline, and kanamycin, respectively. oriV is the origin of replication. trfA and trfB refer to trans-acting replication functions. rlx refers to the relaxation complex site. Tra refers to regions containing genes required for conjugal transfer.

Novel plasmid compositions are provided as vehicles for introduction of exogenous DNA in Gram-negative bacteria, as well as methods for introduction of the plasmid vehicle into Gram-negative bacteria. The plasmid vehicles have a broad host range replication system and are therefore capable of being stably maintained in a wide range of Gram-negative bacteria. The plasmid vehicles also have a broad host range transmissibility in combination with a trans-complementing helper plasmid. Desirably, the plasmid vehicle is relatively small, retaining a complete replication function, while lacking a transfer function but retaining mobilizability with a helper plasmid. In addition, the plasmid should have at least one marker allowing for selection and have unique restriction sites by at least one restriction enzyme, where insertion at the site does not result in the loss of a necessary or desirable function or does result in the loss of a function which allows for selection. The vehicle should not confer hazardous properties to the target host or significantly extend the range of antibiotic resistance. The vehicle will be transmissible with a helper plasmid by biparental and desirably triparental conjugal transfer.

The subject vehicle has a broad host range compatibility. It is capable of being introduced into and replicating in at least 5, preferably at least about 8, more preferably at least 10 different genera of Gram-negative bacteria. Furthermore, it is capable of replicating in a convenient donor microorganism. Particularly useful as the donor organism is Escherichia, more particularly *E. coli*. Of Gram-negative bacteria of interest as recipients are the genera: Pseudomonas; Alcaaligenes; Neisseria; Klebsiella; Serratia; Acinetobacter; Haemophilus; Rhizobium; Azotobacter; Xanthobacter; Salmonella; Shigella; Vibrio; Yersinia; Erwinia; etc.

Desirably, the plasmid vehicle should be relatively small, so as to be able to accept relatively large insertions of exogenous DNA. Usually, the plasmid will be substantially less than about 50 kbp (kilobase pairs), usually below about 40 kbp, more usually less than about 30 kbp and generally greater than about 10 kbp, conveniently from about 10 to 25 kbp, more usually from about 15 to 25 kbp.

The vehicle will be incapable of self-transmissibility. That is, it will lack at least a substantial portion of the DNA sequences involved with conjugal transfer. Normally, at least about 40% by number of nucleotides of the DNA sequences defining the transfer function will be absent, more usually at least about 50%. All of the DNA sequences involved with the transfer function need not be removed and in situations where other essential functions of the plasmid overlap a portion of the DNA sequence involved with the transfer function, this portion will be retained. The less of the transfer function present in the plasmid vehicle, the less likely there is to be recombination with the helper plasmid to recreate an intact transfer function.

While the transfer function must be inoperative, it is essential that the plasmid be capable of mobilization by means of a helper plasmid. That is, the vehicle must be capable of conjugal transfer from a donor to the recipient Gram-negative bacteria. Therefore, the subject plasmid has the mobilizability function.

While not always essential, particularly where the exogenous DNA provides a means for selection, it will normally be desirable to provide a marker as part of the cloning vehicle which allows for selection of transformants. Depending upon the nature of the host, a wide and diverse variety of markers may be employed. Conveniently, antibiotic resistance may be employed which allows for selection of transformants by culturing the cells on a medium containing the particular antibiotic. Antibiotic resistance can be provided to ampicillin, penicillin, tetracycline, kanamycin, etc. Resistance can also be provided to heavy metals. Alternatively, prototrophy can be provided to a auxotrophic host. That is, a host lacking the ability to produce an essential metabolite is transformed with the vehicle which provides the structural genes necessary for the enzymes for producing the metabolite. By culturing the transformants in a culture medium lacking the essential metabolite, the transformants can be selected. Other more sophisticated techniques include providing incompatibility to particular bacteriophage strains, resistance to toxins, changes in morphology, and the like. In some instances, it will be desirable to have a plurality of markers, where one of the markers has a restriction site for insertion of the exogenous DNA. The loss of the property provided by the marker allows for detection of plasmids into which the exogenous DNA has been inserted. Other alternatives exist for monitoring for plasmids having the desired exogenous DNA.

The cloning vehicle will normally have at least one unique restriction site for a restriction enzyme and may have a number of unique restriction sites for the equivalent number of restriction enzymes. The restriction sites will be in non-essential areas of the cloning vehicle, so as not to disturb the functioning of the plasmids. A wide variety of restriction enzymes are known, such as EcoRI, PstI, HindI, II and III, HaeII, KpnI, SalI, HpaI, XhoI, and SmaI, as illustrative but not exhaustive of restriction enzymes.

As already indicated, the vehicle must not be self-transmissible, but must be capable of conjugal transfer by trans-complementation with a helper plasmid. Desirably, the cloning vehicle plasmid should be capable of transmission, where the helper plasmid and the vehicle are initially in different donor cells. The vehicle plasmid will have the necessary function for conjugal mobilizability, as well as a functioning replication system. The functioning replication system may involve one or more genes, which may be contiguous or widely separated.

The exogenous DNA which is introduced will vary depending upon the purpose of the transformation, the nature of the host, the intended use of the host, and the like. The host may be used most simply for amplification of the exogenous DNA, to provide a ready source of the DNA. For the most part, the exogenous DNA will have one or more structural genes, which may be under individual control or polycistronic. The structural genes may be part of an operon, with or without the regulatory genes providing either repression or activation.

The exogenous DNA may be used to augment a natural function of the host, by providing enhanced production of a particular protein e.g. enzyme. The exogenous DNA may be used to modify a property of the host. For example, Pseudomas may be modified to expand the range of hydrocarbon substrates which can be utilized by the bacteria. Nitrogen fixing bacteria, such as Rhizobium may be modified to vary their host specificity. Pathogenic microorganisms may be modified to attenuate or destroy their virulence. Microorganisms may be modified to provide for modification of a product naturally produced by the microorganism. That is, enzymes may be expressed from the exogenous DNA, which will react with a metabolite or catabolite to produce a product of interest. Regulatory functions may be introduced into the microorganism, so as to modify its characteristics or response to changes in its environment. The subject vehicle therefore provides a wide variety of opportunities for producing DNA, augmenting properties of Gram-negative bacteria, modifying properties of Gram-negative bacteria, and producing compounds foreign to a Gram-negative bacterium host.

At the insertion restriction site, it may be desirable to introduce various regulatory signals recognized by the target host. The regulatory signals may include promoters, operators, a CAP binding site, terminator site, a ribosomal start site or terminator site, or the like. Of course, the regulatory signals may be provided on a foreign DNA sequence to be inserted, rather than having them originally present on the vehicle.

The subject vehicle will normally be prepared from an available plasmid, by modification of the plasmid to provide the desired properties. However, synthetic techniques can be used or a combination of synthetic techniques with DNA sequences obtained from naturally occurring plasmids. For broad host range compatability, a convenient plasmid source are those plasmids having broad-host-ranges, such as the P-incompatibility group. Of these, the plasmid RK2 is exemplary. RK2 has undesirable features in being large, greater than 50 kbp, being self-transmissible, and in conferring resistance to several clinically important antibiotics. RK2 is further characterized by having the transfer genes noncontiguous and distributed in widely separated regions. The same is true for the genes involved with DNA replication. RK2 also has the mobilizibility gene overlapping a transfer function gene.

A broad-host-range cloning vehicle lacking self-transmissibility, but being capable of mobilization by trans-complementation with a helper plasmid having a functioning transfer function, can be prepared as follows. It will be assumed that the transfer function genes are widely separated on the plasmid.

A plurality of restriction sites are cleaved by one or more restriction enzymes to provide a plurality of fragments. The restriction sites are chosen so as not to cleave at an essential gene, unless the two fragments are to be reunited at the cleavage site to recreate the intact gene. Also, the cleavage sites are chosen to provide fragments lacking the essential genes, but containing all or part of a gene involving the transfer function. The minimum number of essential genes are the genes involved with replication and mobilizibility.

The fragments are allowed to randomly reunite and the resulting plasmids chosen for retaining the capability of replication and mobilizibility, but not self-transmissibility, as well as retaining at least one restriction site at other than a structural gene.

Since it is desirable to have as little of the transfer function DNA sequences as reasonably feasible, the selected plasmids may be further cleaved, where non-essential DNA and transfer function DNA may be further removed. One convenient technique is to make a single restriction cleavage at or near a transfer function gene and remove the remaining phosphate at the site e.g. with alkaline phosphatase, to prevent recirculation at the site. By cleaving on both sides of the single cleavage site, additional DNA may be removed to reduce the size of the plasmid and recreate ligatable ends for recircularization.

Alternatively, one can choose fragments which lack the transfer function, as well as an essential function. Where the original plasmid has been mapped, the desired DNA sequence defining the gene may be excised and introduced at an appropriate site into the appropriately rejoined fragments.

FIG. 1 shows the plasmid RK2 indicating the sites having the genes conferring antibiotic resistance, the restriction sites, the genes involved with the transmissibility function, which are the shaded areas and the genes involved with the replication function which are the open areas. RK2 was used to prepare an exemplary cloning vehicle, fulfilling the requirements of having a broad host range, capable of mobilization at high frequency with a helper plasmid, conferring limited antibiotic resistance to the target host, having unique restriction sites with at least one restriction enzyme, and being relatively small so as to accommodate large exogenous DNA sequences.

RK2 had been mapped with the DNA replication sites described by Meyer and Helinski (1977), supra, and Thomas and Helinski (1979), supra, while the conjugal mobilizability function was reported by Guiney and Helinski (1979), supra.

Figure 2:
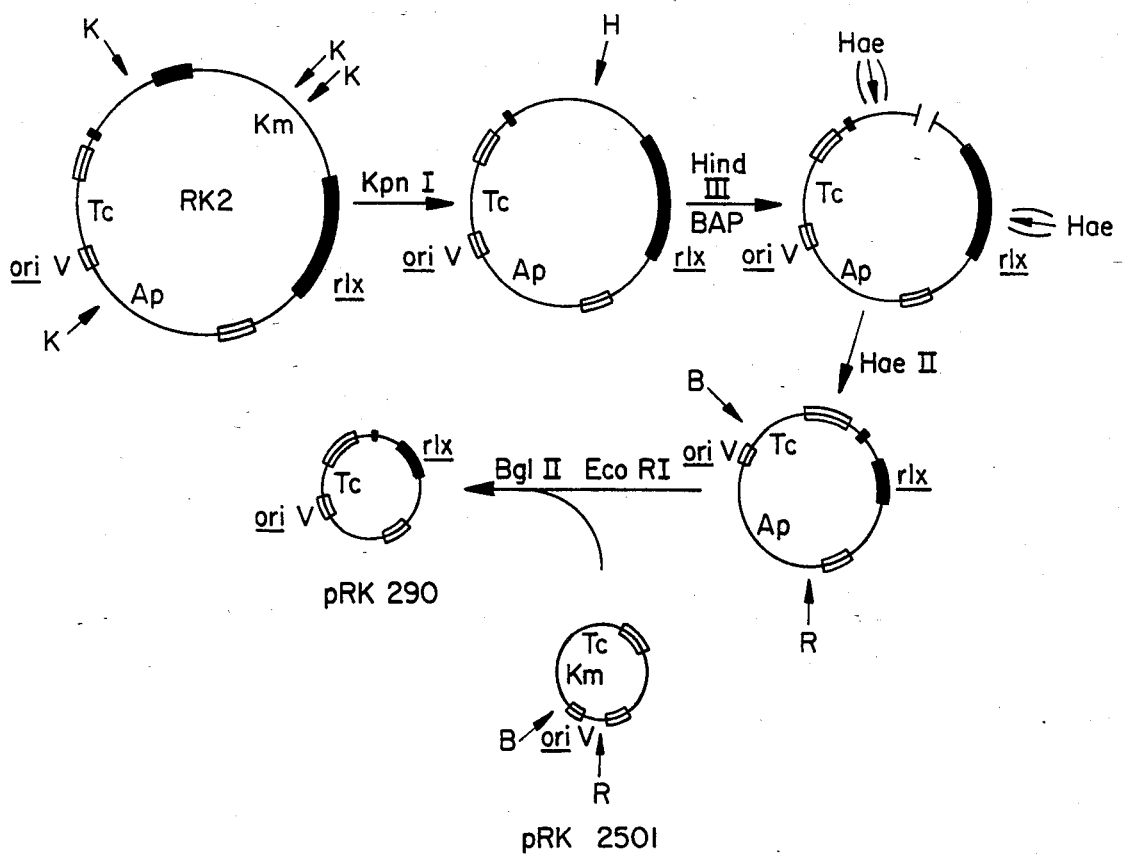
FIG. 2 is the construction of pRK290. Small arrows indicate cleavage sites for restriction enzymes used at each step; for HaeII, the approximate position of cleavages leading ultimately to pRK290 are indicated. BAP refers to treatment with bacterial alkaline phosphatase. Solid bars represent conjugal transfer genes; open bars are essential replication regions. pRK2501 is a previously constructed RK2 deletion derivative containing a HaeII kanamycin fragment that had been inserted in vitro. K-KpnI; H-HindIII; Hae-HaeII; B-Bgl; R-EcoR1.

The manner in which the exemplary cloning vehicle was prepared is shown in FIG. 2. RK2 is cleaved at four positions by KpnI, resulting in four fragments, only two of which carried all the genetic information necessary for autonomous replication and tetracycline resistance. Transformation of E. coli with a total Kpn digest of RK2 DNA and selection for tetracycline resistance yielded transformants containing the two fragments in either of the two possible orientations. DNA with the fragments aligned as in RK2 was treated to remove as much DNA as possible from either side of the single HindIII site without removing rlx or trfA. After digesting the DNA to completion with HindIII followed by treatment with bacterial alkaline phosphatase (BAP) to render it incapable of being covalently re-circularized by DNA ligase, a partial digestion with HaeII was then used to generate pseudo-random cuts on either side of the BAP-treated HindIII site. Whenever at least one cleavage occurred on both sides of the HindIII site, a molecule is generated that could be circularized by DNA ligase. So long as the resulting plasmid retained essential replication regions, such molecules could be detected by transformation. The molecules were screened for retention of the rlx site by monitoring mobilizability with pRK2013. (Figurski and Helinski (1979) Proc. Natl. Acad. Sci. USA 76, 1648–1652). The smallest such derivative was selected, representing a deletion of approximately 11.5 kb of DNA. The next step removed most of the 12.1 kb of DNA between the single EcoR1 site and the single Bgl II site of RK2. For convenience, pRK2501 was employed. (Kahn et al. (1979) Methods in Enzymology, Vol. 68, Recombinant DNA R. Wu, ed. Academic Press, New York). The distance between the single EcoR1 and Bgl II sites in pRK2501 is only 1.1 kb. Their two DNAs were digested jointly with EcoR1 and Bgl II, ligated and used to transform E. coli for tetracycline resistance. Substitution of the appropriate fragment was monitored by screening transformants for sensitivity to ampicillin and kanamycin. The resulting plasmid was 20 kb in size, has two single restriction enzyme sites into which a variety of EcoR1 and Bgl II generated DNA fragments can be cloned successfully and has other enzyme sites within the tetracycline sites, which sites include SmaI and SalI. The molecules specifically lack sites for the enzymes BamHI, HindIII, PstI, KpnI, HpaI, and XhoI, and may be less subject to restriction in those hosts. The copy number of pRK290 in E. coli was found to be similar to that of RK2. For convenience, since interruption of either cloning site does not lead to a detectable change in colony phenotype (e.g. insertional inactivation), it is desirable to treat the restriction enzyme-cleaved vehicle with alkaline phosphatase prior to ligation.

EXPERIMENTAL

Materials and Methods

Bacterial strains.

E. coli HB101 pro leu thi lacy str$^r$ endoI$^-$ recA$^-$r$^-$m$^-$; R. meliloti 102F34 and 104B5 are available from Nitragin Co.; Serratia marcescens MW1 is a clinical isolate reported by D. Guiney; Pseudomonas aeruginosa PAO is also reported by D. Guiney; K. pneumoniae M5A1 is reported by W. Brill; Acinetobacter calcoaceticus is reported by John Ingraham.

Enzymes.

Restriction endonuclease EcoR1 was purified by the inventors; Bgl II was provided by C. Yanofsky; all other restriction enzymes which were employed were obtained from Biolabs, Inc. T4 DNA ligase is available from Bethesda Research Laboratories, Inc. and is used at a concentration of 1 u/ml for ligations. Bacterial alkaline phosphatase is obtained from Miles Laboratories and is dialyzed into 10 mM glycine, pH9.5 and 0.1 mM ZnCl$_2$ for storage. DNA was reacted with this enzyme at 65° C. for 90 min in 10 mM Tris, pH9.5. The reaction was terminated by phenol extraction.

Bacterial Matings.

Matings were performed by mixing $10^9$ cells each of the donor and recipient and filtering the suspension onto 0.45$\mu$ Millipore filters. The filters were incubated at 30° C. on non-selective agar plates for 3 to 6 hours before the cells were resuspended and plated.

Isolation of R. meliloti DNA.

Total DNA from R. meliloti was obtained from 500 ml of stationary-phase cells grown in yeast-mannitol broth (Vincent (1970) In: A Manual for the Practical Study of the Root-Nodule Bacteria, I. B. P. Handbook No. 15, Blackwell Scientific Publications, Oxford, pp.

1-45). Washed cells were resuspended in 50 mM Tris/20 mM EDTA, pH8.0 and lysed with pre-digested pronase (500 μg/ml) and Sarkosyl (1%) for 60 min at 37° C. DNA was purified by equilibrium centrifugation first in neutral CsCl ($\rho=1.70$ g/cc) and then in CsCl-ethidium bromide ($\rho=1.55$ g/cc).

Size Fractionation of R. meliloti DNA.

Total R. meliloti DNA was partially digested with Bgl II to give fragments in the range 10-30 kb. 140 μg of such DNA was heated briefly at 65° C. and layered directly onto a 36 ml 10-40% sucrose gradient in 20 mM Tris, pH8.0, 10 mM EDTA, 50 mM NaCl. Centrifugation was for 18 hrs at 23000 rpm in an SW27 rotor at 25° C. Fractions were monitored for DNA size on a 0.5% agarose gel. Those containing DNA predominantly 12-25 kb in size were pooled and used for construction of the gene bank.

Construction of an R. meliloti Gene Bank.

pRK290 DNA was digested exhaustively with Bgl II and was then treated with bacterial alkaline phosphatase. A small background of transformants was obtained from this DNA, with or without ligation, which probably represented residual uncleaved molecules. Size-fractionated R. meliloti DNA, ligated to this vector, was used to transform HB 101 to tetracycline resistance. The expression time following heat-shock was kept short (approximately 40 min) to avoid the generation of siblings.

The following table, Table 1, shows the frequencies with which pRK290 was transferred into a variety of Gram-negative bacteria as part of the binary plasmid system. The E. coli strain HB101 was chosen as the plasmid host because it is recombination-deficient (rec $A^-$), which is desirable because the vehicle and helper plasmid share regions of homology and HB101 lacks the normal restriction system which might otherwise inactivate unmodified foreign DNA carried as inserts.

TABLE 1

Conjugal Transfer Frequencies of pRK2013/pRK290 Binary Plasmid Systems for Various-Gram Negative Bacteria

| Donor | Recipient | $Tc^R$ Conjugants Recipients | $Km^R/Nm^R$ Conjugants Recipients |
|---|---|---|---|
| E.c. HB101 (pRK2013) | E.c. HB101 rif | — | $8.5 \times 10^{-1}$ |
| E.c. HB101 (pRK290) | E.c. HB101 rif | 0 | — |
| E.c. HB101 (pRK2013, pRK290) | E.c. HB101 rif | $4.0 \times 10^{-1}$ | $8.2 \times 10^{-1}$ |
| E.c. HB101 (pRK2013) | R.m. 104B5 nal | — | $1.7 \times 10^{-7}$ |
| E.c. HB101 (pRK290) | R.m. 104B5 nal | 0 | — |
| E.c. HB101 (pRK2013, pRK290) | R.m. 104B5 nal | $4.6 \times 10^{-2}$ | $8.4 \times 10^{-4}$ |
| E.c. HB101 (pRK2013) + E.c. HB101 (pRK290) | R.m. 104B5 nal | $8.3 \times 10^{-2}$ | $5.6 \times 10^{-4}$ |
| E.c. HB101 (pRK2013) + E.c. HB101 (pRK290) | S.m. nal | $6.6 \times 10^{-2}$ | $2.2 \times 10^{-1}$ |
| E.c. HB101 (pRK2013) + E.c. HB101 (pRK290) | K.p. M5AI | $1.4 \times 10^{-1}$ | $8.8 \times 10^{-1}$ |
| E.c. HB101 (pRK2013) + E.c. HB101 (pRK290) | P.a. PAO nal | $2.6 \times 10^{-1}$ | $8.4 \times 10^{-7}$ |
| E.c. HB101 (pRK2013) + E.c. HB101 (pRK290) | A.c. rif | $8.3 \times 10^{-4}$ | $3.0 \times 10^{-4}$ |

TABLE 1-continued

Conjugal Transfer Frequencies of pRK2013/pRK290 Binary Plasmid Systems for Various-Gram Negative Bacteria

| Donor | Recipient | $Tc^R$ Conjugants Recipients | $Km^R/Nm^R$ Conjugants Recipients |
|---|---|---|---|
| E.c. HB101 (pRK290) | | | |

Tc = Tetracycline; Km = Kanamycin. pRK290 is Tc resistant; pRK2013 is Km resistant.
E.c. = Escherichia coli
R.m. = Rhizobium meliloti
S.m. = Serratia marcescens
K.p. = Klebsiella pneumoniae
P.a. = Pseudomonas aeruginosa
A.c. = Acinetobacter calcoaceticus The first three lines show the high frequency of self-transmissibility displayed by the helper plasmid pRK2013, the absence of self-transmissibility for the vector pRK290, and the high frequency transfer of pRK290 in the binary plasmid system. While the majority of exconjugants selected on tetracycline were found to carry both pRK2013 and pRK290, a sizable portion, approximately 15%, carried only pRK290.

The pattern observed for R. meliloti is quite different from that observed for E. coli. As shown on line 4, pRK2013 has a low rate of transfer indicating the relatively narrow host range of this plasmid. This property is particularly desirable in the helper plasmid to diminish the joint presence of the helper plasmid and the vehicle in the recipient cell. As shown on line 6, pRK290 as a component of the binary plasmid system shows a high rate of transfer into Rhizobium. Based on the observation of some neomycin resistant conjugants, homologous recombination between the helper plasmid and the vehicle is believed to have occurred in the recipient during binary system matings.

As shown in line 7 and subsequent lines, it is not necessary to have pRK2013 and pRK290 together in the same cell at the start of mating for efficient mobilization, it is equally efficient to have triparental matings. Cloned DNA can thus be "stored" in suitable E. coli strains such as HB101 until the time for transfer without necessitating the prior introduction of pRK2013. With all of the Gram-negative bacteria studied, both vehicle and helper plasmid exerted mutual incompatibility leading to a rapid segregational loss of the non-selected plasmid.

Bgl II restriction enzyme fragments of the cellular DNA of R. meliloti 102F34 were sized fractionated on a 10-40% sucrose gradient and fragments 15-20 kb in size were ligated to Bgl II digested pRK290 DNA that had been pre-treated with bacterial alkaline phosphatase and the resulting plasmids used to transform E. coli. Based on a restriction digest pattern of 300 transformants, it was estimated that 929 of 1285 transformants or approximately 72% carried DNA insertions. The average size of the inserts was 19 kb. No instability of the cloned Rhizobium DNAs in HB101 maintained under selected pressure was experienced. Even in the absence of selection, the rate of plasmid loss was generally low, generally less than 1% per generation. Employing colony hybridization (Grunstein and Hogness (1975) Proc. Natl. Acad. Sci. USA 72, 3961-3965) with a known plasmid having nitrogenase structural genes of K. pneumoniae, a single clone was identified which carries as a part of a 26 kb insert a 3.6 kb Bgl II fragment with strong homology to the plasmid pSA30 (Reidel et al.

(1979) Proc. Natl. Acad. Sci. USA 76, 2866–2870; Cannsen et al. (1979) Mol. Gen. Genet. 174, 59–66).

In accordance with the subject invention, novel cloning vehicles are provided having broad host range specificity, without conferring hazardous properties or extended antibiotic resistance to the Gram-negative host. In addition, the vehicles have unique restriction sites for insertion of exogenous DNA, while desirably lacking restriction sites for a wide variety of restriction enzymes endogenous to a number of Gram-negative bacteria. The vehicles are relatively small allowing for insertion of large DNA sequences while still retaining a high frequency of conjugal transmissibility.

Although the foregoing invention has been described in some detail by way of illustration and example for purposes of clarity of understanding, it will be obvious that certain changes and modifications may be practiced within the scope of the appended claims.

What is claimed is:

1. pRK290.
2. A plasmid of from about 10kbp to 30kbp having an RK2 replication system and capable of replication in a plurality of Gram-negative bacteria, lacking self-transmissibility but capable of conjugal transfer by means of a helper plasmid in the same or different donor cell used for said conjugal transfer, wherein said capability for conjugal transfer is derived from RK2 and having at least one marker allowing for selection of transformants.